United States Patent
Bouvy et al.

(10) Patent No.: US 8,946,476 B2
(45) Date of Patent: Feb. 3, 2015

(54) PROCESS FOR THE PREPARATION OF AMINO ACID DERIVATIVES

(75) Inventors: Didier Bouvy, Brussels (BE); Alain Merschaert, Brussels (BE); Véronique Pinilla, Brussels (BE); Joerg Hamann, Köln (DE); Ralf Kanzler, Leverkussen (DE); Antoine Thomas, Lille (FR)

(73) Assignee: UCB Pharma GmbH, Monheim (DE)

( * ) Notice: Subject to any disclaimer, the term of this patent is extended or adjusted under 35 U.S.C. 154(b) by 183 days.

(21) Appl. No.: 13/127,555

(22) PCT Filed: Nov. 6, 2009

(86) PCT No.: PCT/EP2009/007962
§ 371 (c)(1),
(2), (4) Date: Jun. 21, 2011

(87) PCT Pub. No.: WO2010/052011
PCT Pub. Date: May 14, 2010

(65) Prior Publication Data
US 2011/0263899 A1  Oct. 27, 2011

(30) Foreign Application Priority Data
Nov. 7, 2008 (EP) ..................................... 08105749

(51) Int. Cl.
*C07C 231/20* (2006.01)
*C07C 237/22* (2006.01)
*C07C 231/18* (2006.01)

(52) U.S. Cl.
CPC ............. *C07C 231/20* (2013.01); *C07C 231/18* (2013.01); *C07C 237/22* (2013.01)

USPC ........................... 564/158; 564/134; 564/144

(58) Field of Classification Search
USPC ......................................... 564/134, 144, 158
See application file for complete search history.

(56) References Cited

U.S. PATENT DOCUMENTS 5,773,475 A    6/1998  Kohn

FOREIGN PATENT DOCUMENTS

| EP | 1642889 A |   | 4/2006 |
| WO | WO 00/00463 | * | 1/2000 |

OTHER PUBLICATIONS

Choi et al, J. Med. Chem., 1996, 39, 1907-1916.*
Beguin, C. et al., "N-Substituted amino acid N-benzylamides: synthesis, anticonvulsant and metabolic activities", Bioorganic & Medicinal Chemistry, 2004, vol. 12, 3079-3096.
Ebbers et al., "Controlled Racemization of Optically Active Organic Compounds: Prospects for Asymmetric Transformation", Tetrahedron, 1997, 53(28), 9417-9476.

* cited by examiner

*Primary Examiner* — Shailendra Kumar
(74) *Attorney, Agent, or Firm* — McDonnell Boehnen Hulbert & Berghoff LLP

(57) ABSTRACT

The present patent application relates to an alternative process for the preparation of amino derivatives. In particular, the present application relates to an improved process for the manufacture of Lacosamide (LCM), (R)-2-acetamido-N-benzyl-3-methoxypropion-amide, which is useful as an anticonvulsive drug. In a particular aspect, the present invention relates to a process of manufacture of optically enriched (R)-2-acetamido-N-benzyl-3-methoxypropion-amide (I) comprising resolution of 2-acetamido-N-benzyl-3-methoxypropion-amide (II).

24 Claims, No Drawings

PROCESS FOR THE PREPARATION OF AMINO ACID DERIVATIVES

This application is a US national phase of International Application No. PCT/EP2009/007962 filed on Nov. 6, 2009, the disclosure of which is incorporated herein by reference in its entirety.

The present patent application relates to a novel process for the preparation of amino acid derivatives.

In particular, the present application relates to an improved process for the manufacture of Lacosamide (LCM), (R)-2-acetamido-N-benzyl-3-methoxypropion-amide, which is useful as an anticonvulsive drug.

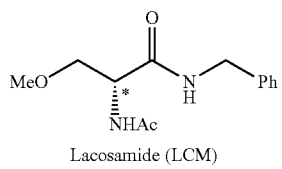 [SMILES: COC[C@@H](NC(C)=O)C(=O)NCc1ccccc1]

Lacosamide (LCM)

LCM has demonstrated antiepileptic effectiveness in different rodent seizure models and antinociceptive potential in experimental animal models that reflect distinct types and symptoms of neuropathic as well as chronic inflammatory pain.

U.S. Pat. No. 5,378,729 describes the preparation of functionalized amino acids by reacting amines with acetylating derivatives of a carboxylic acid under amide forming conditions. U.S. Pat. No. 5,378,729 is however silent on the direct preparation of a single enantiomer of functionalized amino acids, such as Lacosamide.

U.S. Pat. No. 5,773,475 relates to methods of preparation of 'substantially optically pure' Lacosamide, as defined therein, starting from D-Serine. Said method of preparation involves the use of methyl iodide and silver (I) oxide as O-methylation agent which presents the disadvantages of being expensive and leads to partial racemization of the product undergoing the O-methylation. This is a main drawback in terms of industrial productivity of the process.

U.S. Pat. No. 6,048,899 describes variants of the process described in U.S. Pat. No. 5,773,475.

International patent application published as WO 2006/037574 relates to an improved synthesis route to Lacosamide wherein an alternative O-methylation agent to methyl iodide and silver (I) oxide is used, in particular dimethylsulphate.

However the use of an excess of dimethylsulphate as described in WO 2006/037574 may lead to safety or environmental issues when producing Lacosamide on a large scale. Moreover the use of N-protection/N-deprotection steps of the amine moiety may lead to cost and productivity issues for the industrial production of the overall process.

There is therefore a need to find an alternative and improved process for the manufacture of Lacosamide which is competitive, more cost-efficient, leads to an increased productivity and does not present major drawbacks in terms of safety and/or environment.

In a first aspect, the present invention relates to a process of manufacture of optically enriched (R)-2-acetamido-N-benzyl-3-methoxypropion-amide (I) comprising resolution of 2-acetamido-N-benzyl-3-methoxypropion-amide (II) as shown in following scheme 1.

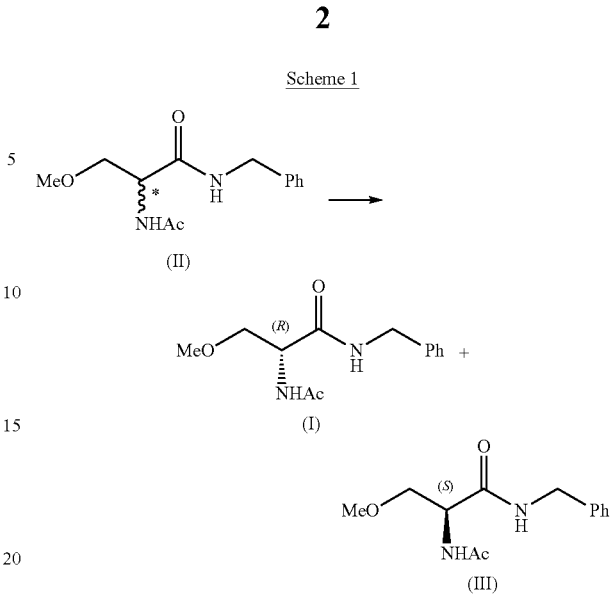

The term "optically enriched" as used herein when referring to a particular compound means that more than 50%, preferably more than 75%, more preferably more than 85%, most preferably more than 94% of the compound has the stereogenic center indicated by (*) in a given configuration (R) or (S).

Therefore, the expression "optically enriched (R)-2-acetamido-N-benzyl-3-methoxypropion-amide" means that more than 50%, preferably more than 75%, more preferably more than 85%, most preferably more than 94% of the compound has the stereogenic center indicated by (*) in configuration (R).

In a second aspect, the present invention relates to a process of manufacture of substantially optically pure (R)-2-acetamido-N-benzyl-3-methoxypropion-amide (I) comprising resolution of 2-acetamido-N-benzyl-3-methoxypropion-amide (II) as shown in scheme 1.

The term "substantially optically pure" as used herein when referring to a particular compound means that at least 95%, preferably at least 96%, more preferably at least 97%, most preferably at least 98%, even most preferably at least 99% of the compound has the stereogenic center indicated by (*) in a given configuration (R) or (S).

Therefore, the expression "substantially optically pure (R)-2-acetamido-N-benzyl-3-methoxypropion-amide" means that at least 95%, preferably at least 96%, more preferably at least 97%, most preferably at least 98%, even most preferably at least 99% of the compound has the stereogenic center indicated by (*) in configuration (R).

The term "resolution" as used herein refers to the separation of a mixture of enantiomers into its corresponding individual enantiomers. The enantiomers may be present in the mixture in various ratios of enantiomer versus the other. Typical ratios of enantiomers according to the present invention range from about 3/97 to 97/3, preferably from about 5/95 to 95/5, more preferably from about 30/70 to 70/30, most preferably from about 40/60 to 60/40, even more preferably from about 45/55 to 55/45.

Particularly, the mixture is a racemic mixture. A racemic mixture as herein defined is a mixture comprising 50% of one enantiomer and 50% of the other enantiomer.

Resolution can be achieved by various methods including conversion to diastereoisomers, differential absorption, chiral recognition, biochemical processes, mechanical separation, kinetic resolution and deracemization as detailed in Jerry March "Advanced Organic Chemistry", fourth edition, Chapter 4, pages 120-125.

Preferably, the resolution according to the present invention is achieved by the differential separation method, more preferably by chiral chromatographic separation using columns packed with a chiral stationary phase (CSP) and a mobile phase. Chiral chromatographic separation may be carried out in batch or by Multi Column Chromatography (MCC).

The term "Multi Column Chromatography" (MCC) as used herein refers to a continuous chromatographic separation technology based on the continuous controlled injection of mixtures onto a series of linked columns packed with a stationary phase. The separated components of the mixture are then withdrawn continuously from the system. This approach would include, but is not limited to, Simulated Moving Bed chromatography mode (SMB mode), or mode where the inlet and outlet ports are shifted asynchronously (such as the Varicol mode) or mode in which inlet and oulet flowrates and/or concentrations are changing in time during the switching period.

The application of the SMB technique for the enantiomeric resolution of racemic mixtures has, for example, been described in the article "Lit mobile simulé. Application à la séparation d'isomères optiques [Simulated mobile bed. Application to the separation of optical isomers]" by R. M. Nicoud, Information Chimie No. 368 (May 1995), pp. 113-115.

The Varicol system is described in international patent application WO 00/25885 and the mode in which fluid flowrates are changing in time during the switching period is described in U.S. Pat. No. 5,102,553.

Hence, in a particular embodiment according to the present invention, resolution of 2-acetamido-N-benzyl-3-methoxypropion-amide (II) is performed by chiral chromatographic separation. In a further particular embodiment, resolution of 2-acetamido-N-benzyl-3-methoxypropion-amide (II) is performed by MCC.

Columns used according to the present invention are generally packed with a CSP which comprises a silica backbone onto which a polymeric chiral selector is coated according to techniques well-known in the art.

The polymeric chiral selector may additionally be immobilized onto the silica backbone which provides to the column, among other advantages, a better resistance to solvents.

In a particular embodiment according to the present invention, chiral chromatographic separation of 2-acetamido-N-benzyl-3-methoxypropion-amide (II) is performed using a column which comprises a polymeric chiral selector which is immobilized onto the silica backbone.

The polymeric chiral selector according to the present invention generally comprises a polysaccharide, for example amylose or cellulose.

Examples of polymeric chiral selector which may be used according to the present invention are cellulose tris(4-methylbenzoate), cellulose tribenzoate, amylose tris(3,5-dimethylphenylcarbamate) cellulose tris(3,5-dimethylphenylcarbamate), cellulose tris(4-methylphenylcarbamate) cellulose tris(3,5-dichlorophenylcarbamate), amylose tris [(S)-α-methylbenzylcarbamate] and cellulose tris(3-chloro-4-methylphenylcarbamate).

In a particular embodiment according to the present invention, chiral chromatographic separation of 2-acetamido-N-benzyl-3-methoxypropion-amide (II) into its enantiomers is performed using cellulose tris(3,5-dichlorophenylcarbamate) immobilized onto a silica backbone as chiral stationary phase.

Examples of mobile phase that may be used according to the present invention are alkanes, such as heptane, hexane, alcohols, such as methanol, ethanol, iso-propanol, n-propanol, acetonitrile, isopropyl acetate, ethyl acetate, dichloromethane, chloroform, ethers, such are methyl t-butyl ether (MTBE), or mixtures thereof.

If mixtures of solvents are used, the ratio will depend upon the type of solvents constituting the mixture, upon the type of column which is used and upon the solubility in those mixtures of the compound to be separated.

Examples of mixtures of solvents according to the present invention are mixtures of dichloromethane and an alcohol or mixtures comprising acetonitrile and an alcohol or mixtures comprising ethyl acetate and an alcohol.

Preferably, mixtures of dichloromethane and an alcohol comprise between 90% and 99% of dichloromethane.

Preferably mixtures of acetonitrile and an alcohol comprise between 90% and 99% of acetonitrile.

Preferably, mixtures of ethyl acetate and alcohol comprise between 90% and 99% of ethylacetate.

Preferred solvents according to the present invention are ethanol, methanol n-propanol, iso-propanol, acetonitrile, dichloromethane and ethyl acetate In a particular embodiment according to the present invention, a mixture of ethyl acetate and methanol is used as mobile phase. In a further embodiment according to the present invention, a mixture of ethyl acetate and methanol in a ratio of 90/10 v:v is used as mobile phase.

In another particular embodiment according to the present invention, acetonitrile is used as mobile phase.

According to the present invention, a productivity of the chiral chromatographic separation greater than 1 Kg of racemic mixture separated per Kg of Chiral Stationary Phase per day is achieved.

In a particular embodiment according to the present invention, a productivity of the chiral chromatographic resolution greater than 2 Kg of racemic mixture separated per Kg of Chiral Stationary Phase per day is achieved.

As shown in scheme 2, in a second aspect, the present invention relates to a process of manufacture of substantially optically pure (R)-2-acetamido-N-benzyl-3-methoxypropion-amide (I) comprising:

(a) resolution of 2-acetamido-N-benzyl-3-methoxypropion-amide (II) into (R)-2-acetamido-N-benzyl-3-methoxypropion-amide (I) and (S)-2-acetamido-N-benzyl-3-methoxypropion-amide (III);

(b) racemisation of (S)-2-acetamido-N-benzyl-3-methoxypropion-amide (III); and (c) further resolution of the resulting 2-acetamido-N-benzyl-3-methoxypropion-amide (II).

Scheme 2

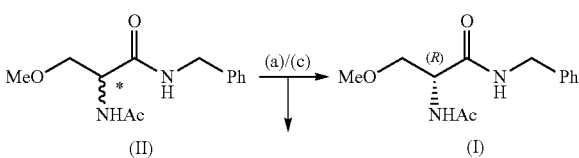

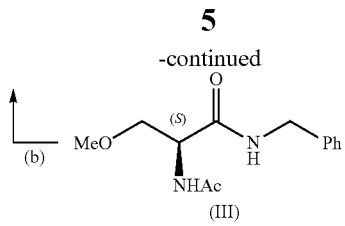

(III)

Steps (a) and (c) are generally performed by chiral chromatographic separation, preferably by MCC.

(R)-2-acetamido-N-benzyl-3-methoxypropion-amide (I) obtained in steps (a) and (c) may be optically enriched or substantially optically pure. Generally, (R)-2-acetamido-N-benzyl-3-methoxypropion-amide (I) obtained in steps (a) and (c) is substantially optically pure. This is particularly advantageous, as it avoids the use of iterative purification steps, such as crystallization which would impact on the productivity of the overall process.

(S)-2-acetamido-N-benzyl-3-methoxypropion-amide (III) obtained in step (a) may be optically enriched or substantially optically pure.

The term "racemisation" as used herein refers to the transformation of an optically enriched enantiomer or a substantially optically pure enantiomer into a mixture consisting of said enantiomer and of the other enantiomer, up to a racemic mixture.

Step (b) may be typically achieved by reacting optically enriched or substantially optically pure (S)-2-acetamido-N-benzyl-3-methoxypropion-amide (III) with a base, with or without acidification of the media.

Examples of bases that can be used according to the present invention are sodium methoxide, potassium hydroxide, sodium hydroxide, potassium carbonate, sodium carbonate, tertiary amines, such as triethylamine, 1,8-Diazabicyclo[5.4.0]undec-7-ene and strong or weakly basic anion-exchange resins, such as AMBERLYST™ A21, AMBERLITE™ IRA400 or IRA410, and the like.

Preferred bases according to the present invention are sodium methoxide, potassium hydroxide, sodium hydroxide, potassium carbonate and sodium carbonate.

When acidification of the media is made, it is preferably performed using a stoechiometric amount of acid with respect to the base to avoid the formation of any degradation products.

Said overall process is particularly advantageous as it avoids any loss of productivity which may sometime occur when using a resolution step. Indeed, often the undesired enantiomer is a by-product of the process which needs to be eliminated from the reaction media. By recycling the undesired enantiomer and performing an additional resolution, for example via chiral chromatography separation, overall yield of process and productivity are increased.

Steps (b) and (c) may be iterated to further increase overall yield of the process.

In a particular embodiment according to the invention, sodium methoxide is used a the base. The racemisation is generally performed in a solvent at a temperature comprised between 20° C. and 80° C., preferably at a temperature comprised between 40° C. and 60° C. More preferably, the reaction is performed at a temperature lower than 60° C. in order to avoid formation of degradation products.

Examples of solvents that may be used for step (b) are alcohol, such as methanol, ethanol, ethers, such as tetrahydrofuran, 2-methyl-tetrahydrofuran or acetonitrile. In a particular embodiment according to the present invention, the solvent is methanol.

2-acetamido-N-benzyl-3-methoxypropion-amide (II) may be prepared by acetylation of 2-amino-N-benzyl-3-methoxypropion-amide (IV) according to methods known to the man skilled in the art, as shown in following scheme 3.

Scheme 3

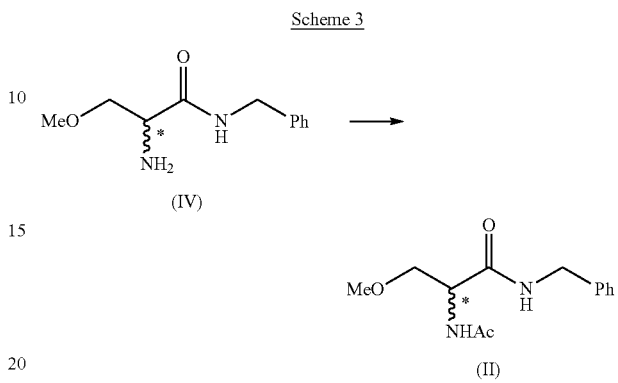

Preferably, the acetylation may be performed using an acetylation agent such as acetic anhydride or acetyl chloride.

A particularly preferred acetylation agent according to the present invention is acetic anhydride.

The acetylation is generally performed in a solvent at a temperature comprised between 20° C. and 70° C. Examples of solvents that may be used for the acetylation are dichloromethane, tetrahydrofuran, ethyl acetate, isopropyl-acetate and isobutyl-acetate.

Preferred solvents are isopropyl-acetate and isobutyl-acetate.

Acetylation is preferably performed at a temperature comprised between 50° C. and 70° C. More preferably, the acetylation is performed at a temperature of about 60° C.

2-amino-N-benzyl-3-methoxypropion-amide (IV) may be prepared according to the method described in scheme 1 of U.S. Pat. No. 6,048,899, incorporated herein as reference, starting from racemic serine, or according to any other method known to the person skilled in the art Alternatively, 2-amino-N-benzyl-3-methoxypropion-amide (IV) may be prepared by ammonolysis of compound (V), wherein X is a leaving group, according to following scheme 4.

Scheme 4

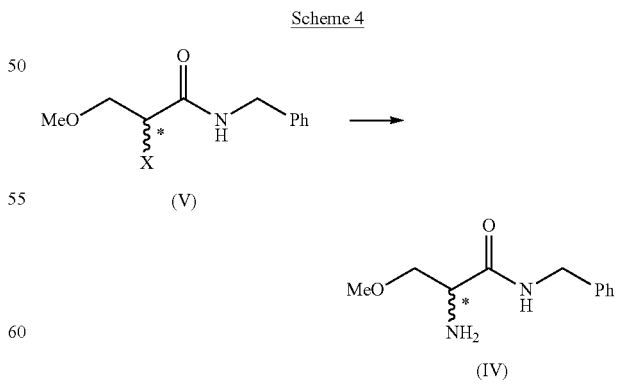

The term "leaving group" as used herein has the same meaning as described in the art (Advanced Organic Chemistry: reactions, mechanisms and structure—Third Edition by Jerry March, John Wiley and Sons Ed.; 1985 page 179), i.e. it represents a group which is part of and attached to a substrate molecule and which in a reaction where the substrate molecule undergoes a displacement reaction (with for example a nucleophile), it (the leaving group) is then displaced.

Examples of a leaving group according to the present invention are halogen or sulfonate groups.

The term "sulfonate group" as used herein represents a group of formula —O—SO$_2$—R$^a$ wherein R$^a$ is an alkyl or an aryl. Preferred sulfonate groups are methanesulfonate, para-toluenesulfonate group or trifluoromethanesulfonate.

Preferably, the leaving group X in compound of formula (V) is a halogen, more preferably bromine or chlorine. Most preferably, X is bromine.

The ammonolysis reaction may be performed according to methods known in the art. For example, the ammonolysis may be performed according to the method described in international patent application published under WO 03/014080.

The ammonolysis according to the present invention is preferably performed with aqueous ammonia in the presence of methanol.

In a particular embodiment according to the present invention an excess of ammonia with respect to compound (V) is used in order to avoid the formation of secondary amine impurities. For example, 20 to 25 molar equivalents of ammonia with respect to compound (V) are used.

After the ammonolysis reaction, 2-amino-N-benzyl-3-methoxypropion-amide (IV) is typically extracted from the reaction media with a solvent. Examples of solvents that may be used for said extraction are isobutylacetate, isopropylacetate, propylacetate, ethyl acetate, 2-methyl-tetrahydrofuran, dichloromethane and toluene.

Preferably isobutylacetate is used as solvent for the extraction of 2-amino-N-benzyl-3-methoxypropion-amide (IV). The extraction with isobutylacetate is preferably performed at a pH higher than 10 and lower than 12, more preferably at a pH between 11 and 12 in order to increase yield of isolation of 2-amino-N-benzyl-3-methoxypropion-amide (IV).

In another embodiment according to the present invention, 2-amino-N-benzyl-3-methoxypropion-amide (IV) may be obtained by performing Gabriel synthesis on compound (V), wherein the leaving group is a halogen. Typical reaction conditions according to this embodiment comprise reacting compound of formula (V) with potassium phtalimide and further reacting the intermediate thereby formed with hydrazine in ethanol as shown in following scheme 5.

Scheme 5

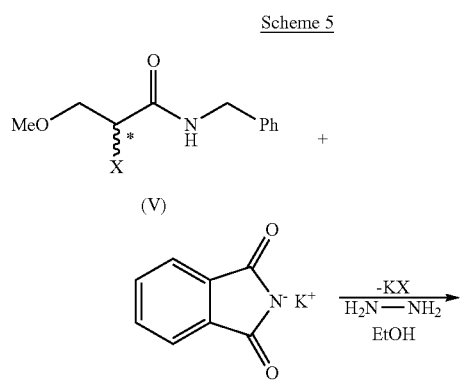

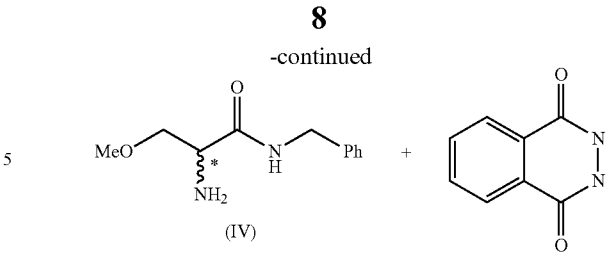

(IV)

Compound of formula (V) may be synthesized according to various methods known in the art. For example, 2-bromo-N-benzyl-3-methoxypropion-amide (Va) may be obtained by applying the method described in Bioorganic and Medicinal Chemistry 2004, 3079.

Alternatively, compounds of formula (V) according to the present invention may be prepared by reacting compound of formula (VI), wherein X is a leaving group as hereabove defined and Y is hydroxy or C$_{1-10}$ alkoxy, with benzylamine, according to following scheme 6.

Scheme 6

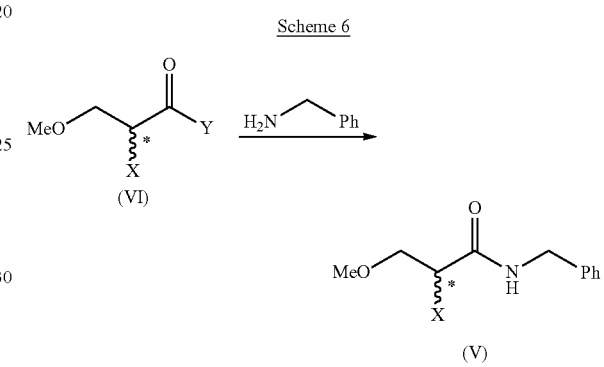

The term "hydroxy", as used herein, represents a group of formula —OH.

The term "alkoxy", as used herein, represents a group of formula —OR$^b$ wherein R$^b$ is C$_{1-10}$ alkyl as defined above.

The term "alkyl", as used herein, is a group which represents saturated, monovalent hydrocarbon radicals having straight (unbranched), branched or cyclic moieties, or combinations thereof.

Reaction conditions depend on the nature of the X and Y groups.

Compound of formula (VI), wherein X is a halogen and Y is a hydroxy group, herein after referred to as compound of formula (VIa), may be converted in situ to a mixed anhydride (VIIIa) (Method A), wherein R is C$_{1-10}$ alkyl or to an acid chloride (VIIIb) (Method B), which intermediates then react with benzylamine, as shown in following scheme 7.

Scheme 7

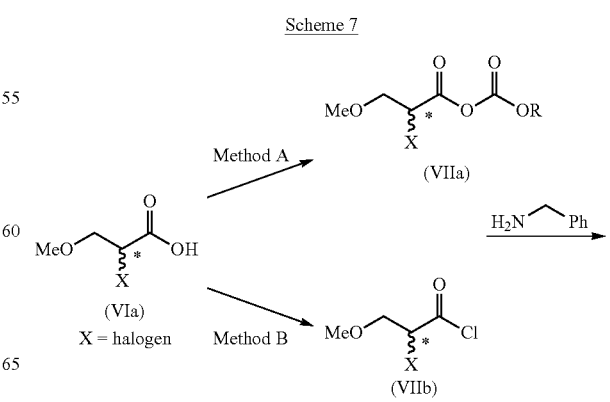

-continued

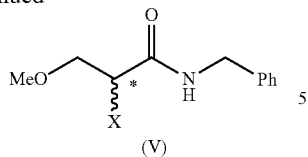

(V)

According to Method A, compound of formula (Via), wherein X is chlorine or bromine, is reacted with an alkyl halo formate, for example ethyl chloroformate or isobutylchloroformate, at a temperature comprised between −10° C. and 10° C., followed by addition of a base, to afford the corresponding mixed anhydride (VIIIa) which is not isolated from the reaction media. The mixed anhydride (VIIIa) is reacted with benzylamine in a solvent at a temperature comprised between −10° C. and 10° C. Preferably said temperature is comprised between −5° C. and 0° C. Examples of solvent that may be used according to this embodiment are dichloromethane, ethylacetate, isobutyl acetate, tetrahydrofuran, toluene, propylacetate, isopropylacetate. In a particular embodiment of the present invention, isobutylacetate or toluene is used as a solvent.

Examples of suitable bases according to the present embodiment are triethylamine, pyridine, N-methylmorpholine, hurling base. In a preferred embodiment of the invention, the base is N-methylmorpholine.

Compound of formula (VIa) that may be used as starting material in Method A are 2-chloro-3-methoxy-propionic acid (VIc) or 2-bromo-3-methoxy-propionic acid (VId).

2-chloro-3-methoxy propionic acid (VIc) is commercially available from various suppliers.

2-bromo-3-methoxy propionic acid (VId) is easily obtainable by reaction of 2,3-bromo propionic acid, or corresponding alkyl esters, with sodium methoxide in methanol, in yields of more than 85%. A method to produce 2-bromo-3-methoxy propionic acid (VId) is for example described by L. L. Wood & V. du Vigneaud, J. biol. Chemistry, 1940, 134, 413.

In a particular embodiment according to the present invention, 2-bromo-3-methoxy propionic acid (VId) may be obtained starting from commercially available 2,3-dibromo ethyl propionate (VIIa) or 2,3-dibromo methyl propionate (VIIb). 2,3-dibromo ethyl propionate (VIIa) or 2,3-dibromo methyl propionate (VIIb) is reacted with sodium methoxide in an organic solvent, preferably methanol, at a temperature lower than 10° C., preferably lower than 0° C., affording 2-bromo-3-methoxy methyl propionate (VIe) which is further reacted in situ with sodium hydroxide, at a temperature comprised between 0° C. and 25° C., preferably at a temperature comprised between 20° C. and 25° C., to afford 2-bromo-3-methoxy propionic acid (VId), after acidification of the mixture with aqueous chlorhydric acid, in a yield comprised between 80% and 90%, according to following scheme 8.

Scheme 8

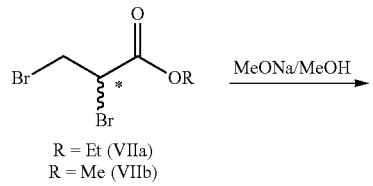

R = Et (VIIa)
R = Me (VIIb)

-continued

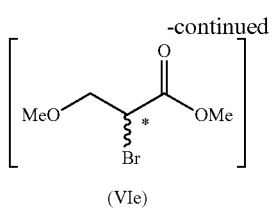

(VIe)

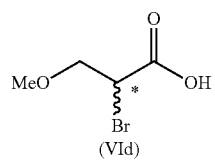

(VId)

Preferably a stoechiometric quantity of sodium hydroxide with respect to 2-bromo-3-methoxy methyl propionate (VIe) is used in order to avoid formation of degradation products.

Hence, both 2-chloro-3-methoxy propionic acid (VIc) and 2-bromo-3-methoxy propionic acid (VId) are easily obtainable from inexpensive starting materials that can be used in the process according to the invention.

2-bromo-3-methoxy propionic acid (VId) is particularly advantageous since it affords corresponding compound of formula (V) in higher yield and higher purity than the corresponding 2-chloro-3-methoxy-propionic acid (VIc).

According to Method B, compounds of formula (VIa), wherein X is chlorine or bromine, may be converted into their corresponding acid chloride according to standard methods known to the person skilled in the art, or by reaction with a compound selected from the group consisting of thionyl chloride, oxalyl chloride, phosphorus trichloride, phosphorus pentachloride, phosphorus oxychloride, phenylphosphonic dichloride and N-chlorosuccinimide, preferably with thionylchloride.

Said Method B may be performed in a solvent selected from dichloromethane, toluene, isobutylacetate or isopropylacetate at a temperature comprises between 20° C. and 60° C.

Example of compound (VIa) that may be used for Method B is 2-chloro-3-methoxy propionic acid (VIc).

Compound of formula (VI), wherein X is a halogen and Y is a $C_{1-10}$ alkoxy group, herein after referred to as compound of formula (VIb), may be either converted into corresponding compound of formula (V) by reaction with benzylamine (Method C), either saponified into the corresponding acid (VIa) which can then undergo any of the transformations (Methods A & B) mentioned in scheme 7 above, as shown here below in scheme 9.

Scheme 9

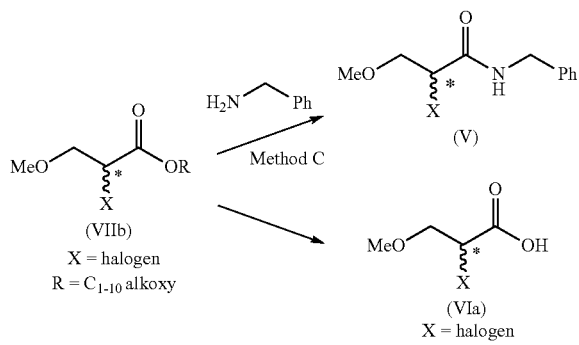

Method A is particularly preferred over Methods B and C since it affords compound (V) in higher yields and with an improved quality.

Hence, in one embodiment, 2-acetamido-N-benzyl-3-methoxypropion-amide (II) according to the present invention may be manufactured by a process comprising the following steps:

(i) reacting a compound of formula (VIa),

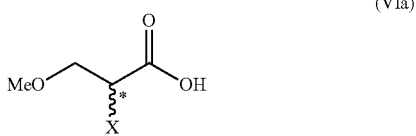

wherein X is a leaving group, with an alkylhaloformiate in the presence of a base and benzylamine;

(ii) performing ammonolysis of compound (V) resulting from step (i), wherein X is as defined in compound (VIa);

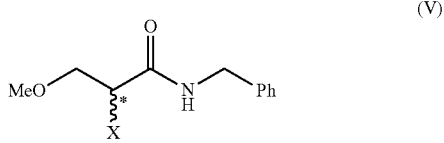

(iii) acetylating compound of formula (IV) thereby obtained

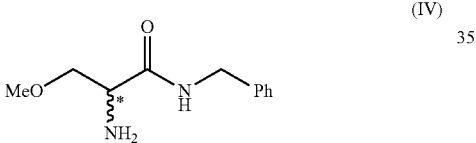

with acetic anhydride in a solvent;

(iv) isolating compound of formula (II).

Step (i) is preferably performed by reacting compound (VIa) with ethylchloroformate or isobutylchloroformate, followed by addition of N-Methyl-Morpholine, which results in the in situ formation of compound (VIIIa).

Hence in a particular embodiment according to the present invention, compound of formula (VIIIa), wherein X is halogen and R is a $C_{1-10}$ alkyl is formed in situ, as shown in scheme 7 above.

Compound of formula (VIIIa) formed in situ then reacts with benzylamine to afford compound of formula (V).

Reaction of step (i) is performed at a temperature comprised between –m10° C. and 10° C. Preferably said temperature is comprised between –5° C. and 0° C.

Step (ii) is preferably performed by treating compound (V) with a molar excess of aqueous ammonia in the presence of methanol. More preferably, 20 to 25 molar equivalents of ammonia with respect to compound (V) are used.

Step (iii) is preferably performed using acetic anhydride as acetylating agent and is at a temperature comprised between 50° C. and 70° C. More preferably, the acetylation is performed at a temperature of about 60° C.

Alternatively, compound of formula (V) may be synthesized by reacting compound of formula (VIIa) or (VIIb) under the conditions mentioned hereabove for the conversion of (VIIa) or (VIIb) into (VId), followed by reaction with benzylamine, without isolation of the intermediate compound (VI).

This provides an advantage in terms of yield and productivity since the overall process has one step less. Examples of compounds of formula (V) according to the present invention are 2-bromo-N-benzyl-3-methoxypropion-amide (Va) and 2-chloro-N-benzyl-3-methoxypropion-amide (Vb).

Examples of compounds of formula (VI) according to the present invention are 2-bromo-3-methoxy propionic acid (VId), 2-bromo-3-methoxy propionic acid methyl ester (VIe), 2-bromo-3-methoxy propionic acid ethyl ester, 2-chloro-3-methoxy propionic acid (VIc), 2-chloro-3-methoxy propionic acid methyl ester, 2-chloro-3-methoxy propionic acid ethyl ester and 2-bromo-3-methoxy propionyl chloride.

Preferably compounds (V), (IV) and (II) are respectively isolated from the reaction media before undergoing any further chemical transformation. Said isolation may be performed by any methods known to the man skilled in the art.

Preferably compound of formula (V) is isolated by crystallization in a mixture of solvents selected from heptane, toluene, isobutylacetate, propylacetate, methyl t-butyl ether. In a particular embodiment, said mixture comprises heptane.

Compound of formula (VI) may be isolated from the reaction media or not.

Preferably compound of formula (II) is isolated by crystallization in a mixture of solvents selected from isobutylacetate, isopropylacetate, propylacetate, 2-Me-tetrahydrofuran and acetonitrile. In a particular embodiment according to the present invention, said mixture comprises isobutylacetate or ethyl acetate.

In a particular embodiment, 2-acetamido-N-benzyl-3-methoxypropion-amide (II) according to the present invention is manufactured by a process comprising the following steps:

(i) reacting 2-bromo-3-methoxy methyl propionic acid (VId),

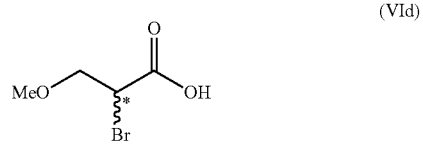

with an alkylchloroformiate in the presence of a base followed by benzylamine;

(ii) reacting resulting 2-bromo-N-benzyl-3-methoxypropion-amide (Va) with aqueous ammonia;

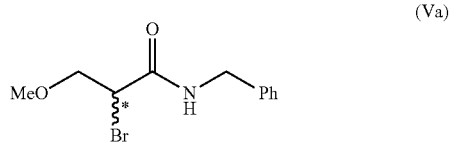 [SMILES: COCC(Br)C(=O)NCc1ccccc1]

(iii) acetylating resulting 2-chloro-N-benzyl-3-methoxypropion-amide (IV) with acetic anhydride in a solvent;

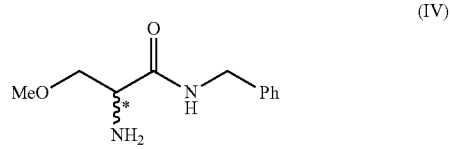 [SMILES: COCC(N)C(=O)NCc1ccccc1]

(iv) isolating compound of formula (II) thereby obtained.

In this particular embodiment 2-bromo-3-methoxy methyl propionic acid (VId) is prepared from commercially available 2,3-dibromo ethyl propionate (VIIa) or 2,3-dibromo methyl propionate (VIIb) as shown in scheme 8 of the present application.

The reaction conditions for steps (i), (ii), (iii) and (iv) are as described here above for Method A of Scheme 7. In a particular embodiment according to the present invention, 2,3-dibromo ethyl propionate (VIIa) may be transformed into 2-bromo-N-benzyl-3-methoxypropion-amide (Va) without isolation of 2-bromo-3-methoxy methyl propionic acid (VId), which is formed in situ.

Hence in a particular embodiment, the present invention relates to a process of manufacture of 2-acetamido-N-benzyl-3-methoxypropion-amide (II) comprising the following steps:

(iii) reacting 2,3-dibromo ethyl propionate (VIIa) or 2,3-dibromo methyl propionate (VIIb)

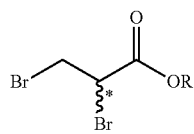

R = Et (VIIa)
R = Me (VIIb)

with sodium methoxide in methanol in the presence of an alkylchloroformiate followed by benzylamine;

(ii) reacting resulting 2-bromo-N-benzyl-3-methoxypropion-amide (Va) with aqueous ammonia;

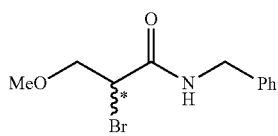

(iii) acetylating resulting 2-chloro-N-benzyl-3-methoxypropion-amide (IV) with acetic anhydride in a solvent;

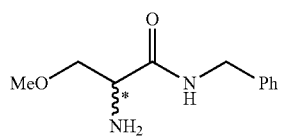

(iv) isolating compound of formula (II) thereby obtained.

In another embodiment according to the present invention, 2-acetamido-N-benzyl-3-methoxypropion-amide (II) is manufactured by reacting 2-acetamido-3-methoxypropionic acid (IX) with an alkyl chloroformiate, preferably ethyl- or isobutylchloroformiate, thereby forming a mixed anhydride which is then reacted with benzylamine.

2-acetamido-3-methoxypropionic acid (IX) may be obtained by acetylation of commercially available O-Methyl-D, L-serine (X) according to following scheme 10.

Scheme 10

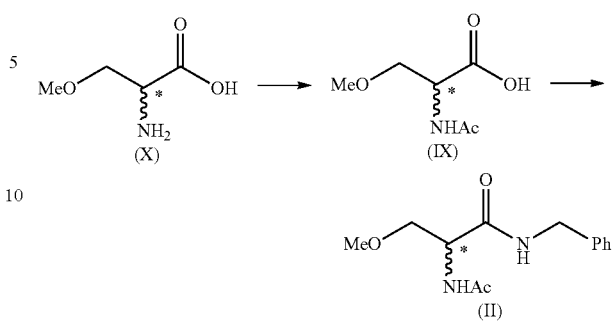

Hence, the present invention also relates to a process for the manufacture of Lacosamide comprising the following steps:
(i) acetylation of O-Methyl-D,L-Serine (X);
(ii) reacting 2-acetamido-3-methoxypropionic acid (IX) thereby obtained with an alkyl chloroformiate followed by benzyl amine;
(iii) isolating compound of formula (II);
(iv) resolution of 2-acetamido-N-benzyl-3-methoxypropion-amide (II) into (R)-2-acetamido-N-benzyl-3-methoxypropion-amide (I) and (S)-2-acetamido-N-benzyl-3-methoxypropion-amide (III);
(v) racemisation of (S)-2-acetamido-N-benzyl-3-methoxypropion-amide (III) thereby obtained.

Step (i) is generally performed using acetic anhydride as acetylating agent in acetic acid, toluene, tetrahydrofuran, 2-methyl-tetrahydrofuran, isobutylacetate, dichloromethane or water, or mixtures thereof. In a particular embodiment according to the present invention said step is achieved in a mixture of tetrahydrofuran and water.

Step (ii) is generally performed in the presence of ethylchloroformiate or isobutylchloroformiate and N-methylmorpholine or triethylamine in tetrahydrofuran, 2-methyl-tetrahydrofuran, toluene, ethyl acetate or dichloromethane.

Alternatively, Step (ii) can be performed in the presence of a catalyst selected from the group consisting of boric acid, phenylboronic acid, 3,4,5-trifluorophenylboronic acid, 2-(N,N-di-isopropylaminomethyl)phenylboronic acid and 2-(N,N-dimethylaminomethyl)phenylboronic acid by refluxing of a solvent selected from the group consisting of toluene, N-methylpyrrolidone and mixtures thereof, tetrahydrofuran, 2-methyl-tetrahydrofuran, cyclopentylmethyl ether, di n-butylether, fluorobenzene using a Dean-Stark apparatus, molecular sieves or sodium sulfate to continuously remove water.

The catalyst according to the present invention may either be soluble in the reaction media or may be solid supported.

In a particular embodiment according to the present invention, a mixture of toluene and N-methylpyrrolidone is used as a solvent. The ratio of the volume of toluene with respect to N-methylpyrrolidone is for example 80/20 or 99/1.

In another embodiment, benzylation of compound of formula (IX) to afford compound of formula (II) may be performed with benzylamine in the presence of di-tert-butyl-dicarbonate ($Boc_2O$) in the presence of pyridine, triethylamine or Hunig's base in a solvent selected from the group consisting of tetrahydrofuran, 2-methyl-tetrahydrofuran, ethyl acetate and dichloromethane.

In a further embodiment, benzylation of compound of formula (IX) to afford compound of formula (Ii) may be performed with benzylamine in the presence of n-propanephosphonic acid anhydride (T3P®) in the presence of triethylamine or Hunig's base in a solvent selected from ethyl acetate, tetrahydrofuran, dichloromethane and 2-methyl-tetrahydrofuran.

In yet another embodiment, benzylation of compound of formula (IX) to afford compound of formula (II) may be performed with benzylamine in the presence of dicyclohexyl—(DCC) or diisopropylcarbodiimide (DIC) in a solvent selected from the group consisting of tetrahydrofuran, ethyl acetate and dichloromethane.

In yet another embodiment, benzylation of compound of formula (IX) to afford compound of formula (II) may be performed in neat benzylamine in the presence of hexamethyldisalazane (HMDS).

In yet another embodiment, benzylation of compound of formula (IX) to afford compound of formula (II) may be performed by heating a solid 1:1 mixture of (IX) with benzylamine above 130° C.

Catalysts used for the benzylation step according to the present embodiment of the invention may be either soluble in the reaction or supported on a solid.

This method is particularly advantageous as it comprises few chemical steps from starting material up to compound (II).

In a particular aspect, the present invention relates to a process for the preparation of Lacosamide comprising the following steps:

(i) reacting a compound of formula (VIa),

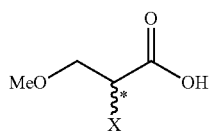

(VIa)

wherein X is a leaving group, with an alkylhaloformiate in the presence of a base and benzylamine;

(ii) performing ammonolysis of compound (V) resulting from step (i), wherein X is as defined in compound (VIa);

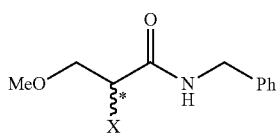

(V)

(iii) acetylating compound of formula (IV) thereby obtained

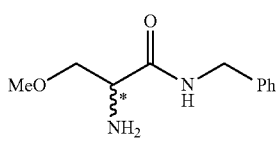

(IV)

with acetic anhydride in a solvent;
(iv) isolating compound of formula (II); and
(v) performing resolution of 2-acetamido-N-benzyl-3-methoxypropion-amide (II) into (R)-2-acetamido-N-benzyl-3-methoxypropion-amide (I) and (S)-2-acetamido-N-benzyl-3-methoxypropion-amide (III).

In an even more particular aspect, the present invention relates to a process of manufacture of (R)-2-acetamido-N-benzyl-3-methoxypropion-amide (I) comprising the following steps:

(i) reacting a compound of formula (VIa),

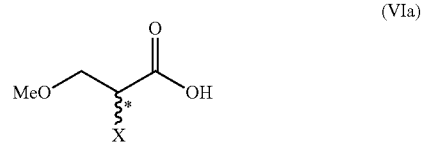

(VIa)

wherein X is a leaving group, with an alkylhaloformiate in the presence of a base and benzylamine;

(ii) performing ammonolysis of compound (V) resulting from step (i), wherein X is as defined in compound (VIa);

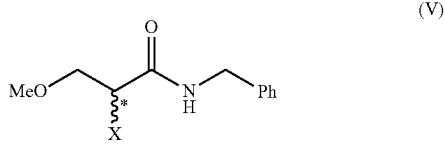

(V)

(iii) acetylating compound of formula (IV) thereby obtained

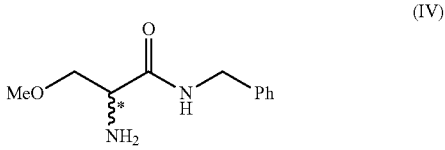

(IV)

with acetic anhydride in a solvent;
(iv) isolating compound of formula (II);
(v) resolution of 2-acetamido-N-benzyl-3-methoxypropion-amide (II) into (R)-2-acetamido-N-benzyl-3-methoxypropion-amide (I) and (S)-2-acetamido-N-benzyl-3-methoxypropion-amide (III);
(vi) racemisation of (S)-2-acetamido-N-benzyl-3-methoxypropion-amide (III) thereby obtained; and
(vii) further resolution of the resulting 2-acetamido-N-benzyl-3-methoxypropion-amide (II).

Step (iv) is preferably performed by crystallization in a solvent selected from the group consisting of toluene, ethyl acetate, isobutylacetate, isopropylacetate, acetonitrile, 2-methyl-tetrahydrofuran and mixtures thereof.

Compound (II) is thereby preferably obtained with a purity of at least about 98% measured by HPLC, more preferably with a purity of at least about 99%, most preferably with a purity of at least about 99.5%

Step (v) in the two embodiments detailed here above is preferably performed by chiral chromatographic separation. In one embodiment according to the present invention, the chiral chromatographic separation is performed by MCC.

Said separation is preferably performed using a CSP which comprises a polysaccharide chiral selector coated or immobilized on a silica backbone according to techniques well-known in the art and a mobile phase, as detailed here above in the specification.

In a particular embodiment according to the invention, the polymeric chiral selector is selected from cellulose tris(4- methyl benzoate), cellulose tribenzoate, amylose tris(3,5-dimethylphenylcarbamate) cellulose tris(3,5-dimethylphenylcarbamate), cellulose tris(4-methylphenylcarbamate) cellulose tris(3,5-dichlorophenylcarbamate), amylose tris [(S)-α-methylbenzylcarbamate]and cellulose tris(3-chloro-4-methylphenylcarbamate) and the solvent is selected from alkanes, such as heptane, hexane, alcohols, such as methanol, ethanol, iso-propanol, n-propanol, acetonitrile, isopropyl acetate, ethyl acetate, dichloromethane, chloroform, ethers, such are methyl t-butyl ether (MTBE) or mixtures thereof.

In a preferred embodiment according to the present invention, the separation in step (v) is performed using cellulose tris(3,5-dichlorophenylcarbamate) immobilized on a silica backbone as polymeric chiral selector and a mixture of ethyl acetate and methanol in a 90/10 v:v ratio was used as mobile phase.

Step (vi) is preferably performed by reacting compound (III) with sodium methoxide, followed by stoechiometric acidification.

The temperature of the racemisation is preferably lower than 60° C.

In the process of manufacture of Lacosamide, the substantially optically pure (R)-2-acetamido-N-benzyl-3-methoxypropion-amide (I) obtained after the resolution step may be further crystallized for purification purposes. This crystallization is preferably performed in ethyl acetate.

In a particular embodiment according to the present invention, the crystallization is initiated by seeding the crystallization media with substantially optically pure (R)-2-acetamido-N-benzyl-3-methoxypropion-amide (I). In this particular embodiment the seeding is be performed at a temperature comprises between 60° C. and 80° C., preferably at a temperature comprised between 65° C. and 75° C.

The process according to the present invention is particularly advantageous over known processes of manufacture of Lacosamide because:
  the starting materials are readily available;
  it does not require the use of protecting agent for amine functions present in synthetic intermediates which generates additional protection-deprotection process steps and thus increases costs of production;
  It does not use reagents which are detrimental to the environment;
  the undesired enantiomer (Ill) may ultimately be recycled into Lacosamide, thereby increasing the overall productivity of the process.

In another embodiment, the present invention relates to a process of manufacture of substantially optically pure (R)-2-acetamido-N-benzyl-3-methoxypropion-amide (I) comprising the following steps:
  (i) resolution of 2-amino-N-benzyl-3-methoxypropion-amide (IV);
  (ii) acetylation of (R)-2-amino-N-benzyl-3-methoxypropion-amide (IVa) thereby obtained with acetic anhydride; and
  (iii) crystallization of (R)-2-acetamido-N-benzyl-3-methoxypropion-amide thereby obtained.

In the present embodiment, resolution is preferably performed by diastereosomeric salt formation by reacting compound of formula (IV) with an acid selected from the group consisting of R)-(−)-mandelic acid, (S)-(+)-mandelic acid, (D)-(+)-malic acid, (L)-(−)-malic acid, (+)-O,O'-dibenzoyl tartaric acid, (L)-N-acetyl-alanine and (D)-N-acetyl-leucine, i.e. 'Conversion to diastereoisomers" method described in Jerry March in "Advanced Organic Chemistry", fourth edition, Chapter 4, pages 120-125.

Resolution is preferably performed in a solvent selected from the group consisting of acetone, methanol, ethanol, 1-propanol, methyl-tert-butyl-ether, heptane, cyclohexane, methylethylketone, isopropylacetate and mixtures thereof.

Resolution is preferably performed at a temperature comprised between 20° C. and 60° C. followed by cooling at a temperature comprised between 0° C. and 20° C.

(R)-2-acetamido-N-benzyl-3-methoxypropion-amide is further crystallized to afford substantially optically pure (R)-2-acetamido-N-benzyl-3-methoxypropion-amide. Said crystallization is iterated until (R)-2-acetamido-N-benzyl-3-methoxypropion-amide is obtained in the desired optical purity.

Alternatively the resolution step may be performed by chiral chromatographic separation using different absorption methods, more preferably using chiral chromatographic separation carried out in batch or in MCC (Multi Column Chromatography) including SMB (simulated moving bed) mode or mode where the inlet and outlet ports are shifted asynchronously or mode in which inlet and oulet flowrates and/or concentrations are changing in time during the switching period, as detailed here above in the specification for 2-acetamido-N-benzyl-3-methoxypropion-amide (II).

2-amino-N-benzyl-3-methoxypropion-amide (IV) used in the present embodiment may be prepared according to any of the methods described here above in the specification.

All process steps mentioned here above, and particularly processes of manufacture of compound (II), including synthesis and extraction of the materials may be individually or collectively performed in batch mode or according to a continuous process, using for example micro-reactors.

EXAMPLES

The following examples are provided for illustrative purposes only and are not intended, nor should they be construed, as limiting the invention in any manner. Those skilled in the art will appreciate that routine variations and modifications of the following examples can be made without exceeding the spirit or scope of the invention.

NMR spectra are recorded on a Bruker 400 MHz spectrometer as solutions in deuterated chloroform ($CDCl_3$). Chemical shifts are expressed in parts per million (ppm, δ) downfield from tetramethylsilane and are referenced to the deuterated solvent ($CDCl_3$).

$^1H$ NMR data were reported in the order of chemical shift, multiplicity (s, singlet; d, doublet; t, triplet; q, quartet; m, multiplet; app, apparent and/or multiple resonance), coupling constant (J) in hertz (Hz) and number of protons.

High Performance Liquid Chromatography (HPLC) spectra are recorded on an Alliance Waters 2695 equipped with the HPLC spectra were recorded on an Alliance Waters 2695 equipped with an Atlantis T3 3 microns column (4.6×100 mm), detecting at 200 nm—starting solvent composition=water: 90% vol/water+1% H3PO4:10% vol; final solvent composition=water+1% H3PO4:10% vol/acetonitrile:90% vol in 6 minutes followed by re-equilibration period of 1 min to the initial solvent composition.

Chiral HPLC are recorded on a Merck-Hitachi L-7100 equipped with a Daicel Chiralpak OJ-H® 5 μm. Eluent is a mixture of heptane/ethanol 96/4 with a flow of 2 ml/min.

Gas chromatography (GC) spectra are recorded on an Agilent 6890 series equipped with an Altech GC DB-5MS (15 m×0.25 mm) column. The oven is heated at 50° C. with a 1.5 mL/min helium flow and a FID detector heated at 300° C.

Mass spectroscopy (MS): API spectra were performed using a FINNIGAN (San Jose, Calif., USA) LCQ ion trap mass spectrometer. APCI source operated at 450° C. and the capillary heater at 160° C. The ESI source operated at 3.5 kV and the capillary heater at 210° C.

Example 1

Preparation of Lacosamide Starting from 2,3-dibromo ethyl propionate (VII)

Example 1a

Preparation of 2-bromo-3-methoxy propionic acid (VId) from 2,3-dibromo ethyl propionate (VII)

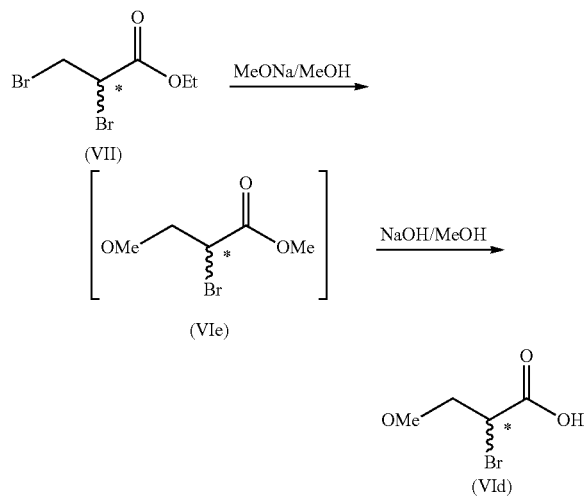

In a dry equipment under nitrogen, 2,3-dibromo ethyl propionate (VII) available commercially (1 equiv) is dissolved in 4 volumes of dry methanol and the solution is cooled to −10° C. under stirring. A 25% w/w solution of sodium methoxide in methanol (1.1 equiv) is slowly added such as the temperature is maintained below −5° C. After addition, the mixture is allowed to warm to room temperature and the reaction is post-stirred at 20° C. for 1 hour.

20% aqueous sodium hydroxide (1 equiv) is added slowly at a temperature maintained below 23° C. The reaction mixture is then stirred at 20° C. for 1 hour.

37% aqueous HCl is slowly added till pH 5-6 and the reaction mixture concentrated to the minimal agitation volume, i.e. 1 volume vs compound (VII), under vacuum at a temperature of maximum 40° C.

37% aqueous HCl is added until the pH is 2 and the salty residue is taken in a minimum amount of water (~0.6 volumes) to get a solution and the compound (VId) is extracted with isobutylacetate (3×2 volumes). The organic layer is evaporated to ca. 4 volumes affording a solution of 2-bromo-3-methoxy propionic acid (VId).

Example 1b

Preparation of 2-bromo-N-benzyl-3-methoxypropion-amide (Va) from 2-bromo-3-methoxy propionic acid (VId)

Method A

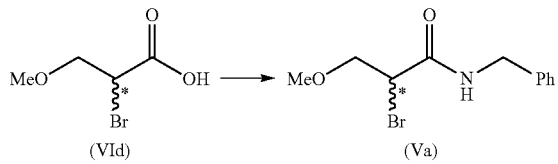 [SMILES: COCC(Br)C(=O)O ; COCC(Br)C(=O)NCc1ccccc1]

The solution of 2-bromo-3-methoxy propionic acid (VId) (1 equiv, amount calculated by w/w assay) in isobutylacetate from previous step is cooled to −5° C. under stirring. Ethyl chloroformate (1.1 equiv) is added so as to obtain a mass temperature between −5 and 0° C. The addition funnel is rinsed with 0.1 volume isobutylacetate. N-methylmorpholine (1.1 equiv) is added slowly so as to obtain a mass temperature between −5 and 0° C. The addition funnel is rinsed with 0.1 volume isobutylacetate. The solution is post-stirred for 30 min at −5/0° ° C. Benzylamine (1.1 equiv) is added so as to obtain a mass temperature between −5° C. and 0° C. The addition funnel is rinsed with 0.25 volume isobutylacetate. The reaction mixture is allowed to warm up to 25-30° C. and post-stirred for about 1 hour (HPLC area of (VId) lower than 0.2%).

1 volume of water with respect to the initial solution of (VId) is added and the mixture stirred for 15 min. The aqueous layer is separated and the organic layer washed with water (0.5 volume). The solution is concentrated to ca. 2.5-3 volumes of isobutylacetate at 40° C. under vacuum and seeded with compound (Va) at 30-35° and the suspension cooled to room temperature till the crystallization is well initiated. At the same temperature, about 5 volumes of heptane are slowly added. Then the suspension is progressively cooled to −10° C. The crystals are filtered, washed with chilled 1:2 iButOAc/heptane (1 volume) and heptane (2 volumes) and dried at 40° C. under vacuum. 2-bromo-N-benzyl-3-methoxypropion-amide (Va) is isolated with a yield of 70% (vs ethyl dibromopropionate used in Step 1).

(Va): mp 74-75° C.; $^1$H NMR (CDCl$_3$) δ 3.43 (s, OCH$_3$), 3.87 (dd, J=5.0, 10.7 Hz, CHH'O), 3.95 (dd, J=4.6, 10.7 Hz, CHH'O), 4.43-4.50 (m, CH and CH$_2$Ph), 6.93 (br s, NH), 7.24-7.37 (m, 5 PhH); $^{13}$C NMR (CDCl$_3$) 44.0, 47.9, 59.2, 73.6, 127.4, 127.5, 128.7, 137.4, 167.0 ppm.

Method B

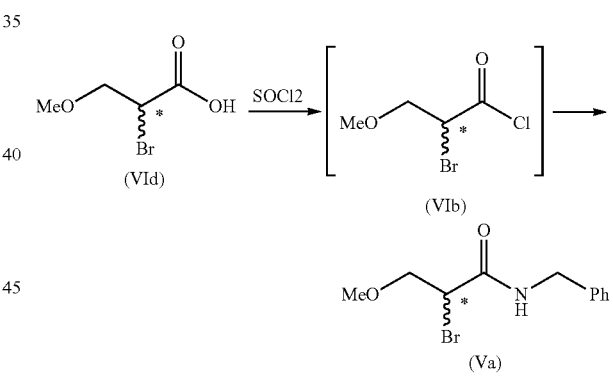

In a reaction vessel, equipped with a mechanical stirrer, an addition funnel and a thermometer probe, add at 20 C, 1 equiv of (VId), 8 volumes of toluene and 0.1 equiv of dimethylformamide. At 20° C., add dropwise 1.1 equiv of SOCl$_2$ within 15 minutes. Stirr for 20 minutes at 20° C. after the addition. The reaction mixture is then cooled to −10° C. and 2 equiv of triethylamine are added dropwise within 15 minutes. Heat to 20° C. and stirr for 20 minutes at 20° C. Cool the reaction mixture to −10° C., add dropwise 1 equiv of benzylamine and allow the reaction mixture to warm to 20° C. 1 volume of water with respect to the initial solution of VId is added and the mixture stirred for 15 min. The aqueous layer is separated and the organic layer washed with water (0.5 volume). The solution is concentrated to ca. 2.5-3 volumes of isobutylacetate at 40° C. under vacuum and seeded with compound (Va) at 30-35° and the suspension cooled to room temperature till the crystallization is well initiated. At the same temperature, about 5 volumes of heptane are slowly added. Then the suspension is progressively cooled to −10° C. The crystals are filtered, washed with chilled 1:2 iButOAc/heptane (1 volume) and heptane (2 volumes) and dried at 40° C. under vacuum.

Example 1c

Preparation of Preparation of 2-bromo-N-benzyl-3-methoxypropion-amide (Va) from 2,3-dibromo ethyl propionate (VII)

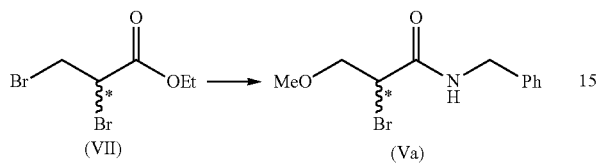

5.2 g of 2,3-dibromo ethyl propionate (VII) were dissolved with 20 ml Methanol. At a temperature of between −10° C. and −5° C. within 5 minutes, 4.08 ml of a sodium methanolate solution 30% in Methanol were added. The solution was stirred for 10 minutes at 0° C. to 5° C. 10.9 ml of benzyl amine was then added to the mixture which was stirred for 2 h at room temperature. Methanol was evaporated and the residue was taken up in 100 ml 1 M hydrochloric acid. The built up precipitate was extracted with 50 ml of dichloromethane. Dichloromethane was then evaporated from the media until dryness.

Residue: 4.2 g colourless crude

The residue was re crystallised from a mixture from 6 ml methyl tert-butyl ether and 3 ml of n-heptane and 2.79 were isolated.

Yield=51.26%; LCMS: 97.9% [M+H]=272

Example 1d

Preparation of 2-amino-N-benzyl-3-methoxypropion-amide (IV) by ammonolysis of 2-bromo-N-benzyl-3-methoxypropion-amide (Va)

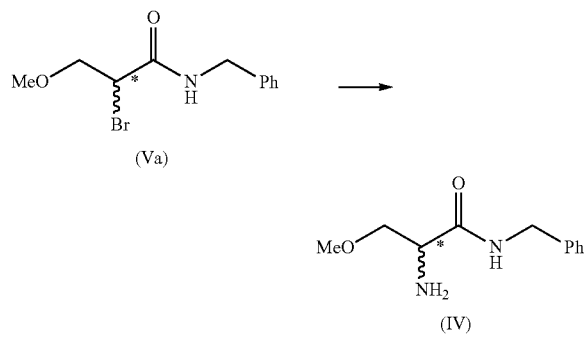

2-bromo-N-benzyl-3-methoxypropion-amide (Va) (1 equiv) is dissolved in 6 volumes of 28% aqueous ammonia and 2 volumes of methanol. The solution is heated to 100° C. under stirring for about 2 hours at a pressure of 7 bar. The reaction mixture is concentrated under vacuum at 50-60° C. till precipitation of the salts. At room temperature the minimum amount of water is added in order to solubilise the salts. The pH of the solution is adjusted to 12 with 50% aqueous sodium hydroxide and 2-amino-N-benzyl-3-methoxypropion-amide (IV) is extracted with isobutyl acetate (3 to 4×2 volumes). The combined organic layers are dried azeotropically. The salts that precipitate after drying are eliminated by filtration and compound (IV) is used directly in the next step without further purification.

The reaction can be monitored by HPLC. LC-MS (+Cl) (rel intensity) 210 (12), 209 (M$^+$+1, 100).

A sample is evaporated to dryness (oil): $^1$H NMR (CDCl$_3$) d 1.74 (br, s, NH$_2$), 3.34 (s, OCH$_3$), 3.53-3.61 (m, CHCH$_2$), 4.36-4.48 (m, CH$_2$NH), 7.22-7.33 (m, 5 PhH), 7.75-7.86 (m, NH).

Example 1e

Preparation of 2-acetamido-N-benzyl-3-methoxypropion-amide (II) by acetylation of 2-amino-N-benzyl-3-methoxypropion-amide (IV)

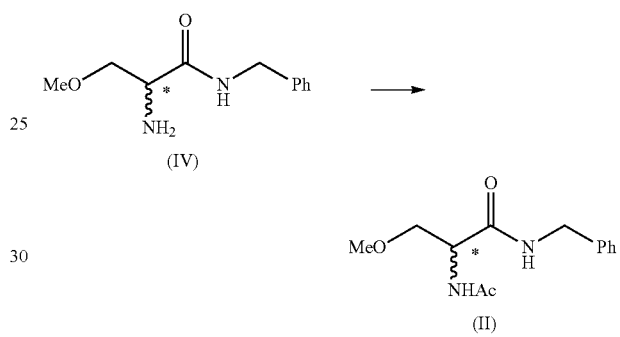

The combined organic layers in the preceding step are adjusted to 7 volumes with respect to the initial amount of 2-bromo-N-benzyl-3-methoxypropion-amide (Va) used in the preceding step and the temperature of the solution is adjusted to 60° C. 1 equivalent (with respect to the initial amount of 2-bromo-N-benzyl-3-methoxypropion-amide (Va) used in the preceding step) of acetic anhydride is added dropwise while the temperature is maintained below 70° C.

0.5 volume of water is added and the mixture stirred for 15 minutes. The aqueous layer is decanted and discarded and the same operation is repeated.

The solution is then seeded with 2-acetamido-N-benzyl-3-methoxypropion-amide (II) and slowly cooled to 0° C. The crystals are filtered, washed with 2 volumes of isobutylacetate at 0° C. and dried under vacuum at 40° C.

2-acetamido-N-benzyl-3-methoxypropion-amide (II) is thereby isolated in 80% yield.

(II): mp 122-123° C.; $^1$H NMR (CDCl$_3$): δ 2.02 (s, C(O)CH$_3$), 3.37 (s, OCH$_3$), 3.42 (dd, J=7.8, 9.0 Hz, CHH'OCH$_3$), 3.80 (dd, J=4.0, 9.0 Hz, CHH'OCH$_3$), 4.47 (d, J=6.0 Hz, NHCH$_2$), 4.49-4.56 (m, CH), 6.41 (br d, J=6.0 Hz, NH), 6.73 (br s, NH), 7.22-7.37 (m, 5 PhH)

Example 1f

Resolution of 2-acetamido-N-benzyl-3-methoxypropion-amide (II) Into (R)-2-acetamido-N-benzyl-3-methoxypropion-amide (I) and (S)-2-acetamido-N-benzyl-3-methoxypropion-amide (III)

Method A

A feed solution of 2.1 kg of 2-acetamido-N-benzyl-3-methoxypropion-amide (II) in acetonitrile is prepared and stirred under nitrogen until complete dissolution is achieved. The solution is continuously injected in an SMB system which is equipped with six identical columns of 12.46 cm length and 4.8 cm internal diameter, in a 1-2-2-1 configuration. Each column contains 125 g of a Chiral stationary phase comprising cellulose tris(3,5-dimethylphenylcarbamate) coated onto the silica backbone and the enantiomers are separated using acetonitrile as the mobile phase.

Substantially optically pure (R)-2-acetamido-N-benzyl-3-methoxypropion-amide (I) is extracted from the stream and obtained with an enantiomeric excess greater than 99%.

Method B

A feed solution of 12 kg of 2-acetamido-N-benzyl-3-methoxypropion-amide (II) in Ethyl acetate-MeOH (90/10) is prepared and stirred under nitrogen until complete dissolution is achieved. The solution is continuously injected in an SMB system which is equipped with six identical columns of 12.4 cm length and 4.8 cm internal diameter, in a 1-2-2-1 configuration. Each column contains 125 g of a Chiral stationary phase comprising cellulose tris(3,5-dichlorophenylcarbamate) immobilized onto the silica backbone and the enantiomers are separated using Ethyl acetate-MeOH (90/10) as the mobile phase.

Substantially optically pure (R)-2-acetamido-N-benzyl-3-methoxypropion-amide (I) is extracted from the stream and obtained with an enantiomeric excess greater than 99%.

Example 1g

Racemisation of (S)-2-acetamido-N-benzyl-3-methoxypropion-amide (III) Into 2-acetamido-N-benzyl-3-methoxypropion-amide (II)

To a solution of (S)-2-acetamido-N-benzyl-3-methoxypropion-amide (III) isolated in the preceding step, in 5 volumes of methanol, 0.05 equivalents of sodium methoxide are added under nitrogen flush. The mixture is warmed up to 60° C. for 8 h followed by a cooling down to 10° C.

The mixture is quenched with a 0.05 equivalent of an aqueous solution of HCl while maintaining the mass temperature at about 20° C. The methanol is distilled under atmospheric pressure until about 1 volume of solvent remains. An azeotropic distillation with 9 volume of isopropylacetate is then performed. The distillation is carried out by continuous addition of isopropylacetate in order to maintain a total of 10 volumes (about 5 volumes are distilled to achieve a residual level of MeOH<0.1% by GC).

The mixture is cooled down to 60° C. and is washed with water. The residual water in the organic layer is removed by azeotropic distillation with isopropylacetate according to the same method as mentioned here above.

The solution is cooled down to 0° C. for crystallization. The suspension is filtered and the cake is washed with isopropylacetate. The solid is dried under reduced pressure at 40° C.

2-acetamido-N-benzyl-3-methoxypropion-amide (II) is obtained with a yield of 74%.

Conditions of example 1e are again applied to 2-acetamido-N-benzyl-3-methoxypropion-amide (II) here obtained.

Example 2

Preparation of 2-amino-N-benzyl-3-methoxypropion-amide (IV) from 2-chloro-3-methoxy propionic acid (VIc)

Example 2.1

Preparation of N-benzyl-2-chloro-3-methoxy-propionamide (Vb) from 2-chloro-3-methoxy propionic acid (VIc)

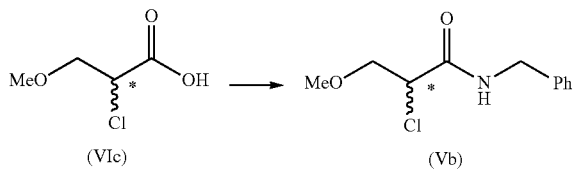

5.54 g (0.04 mol) of 2-chloro-3-methoxy propionic acid (VIc) is dissolved in 50 ml dichloromethane The solution is cooled to −5° C. 6.24 ml (0.048 Mol) isobutyl chloroformiate are added within 5 minutes. The solution is cooled to −10° C. Within 5 minutes 5.28 ml (0.048 Mol) N-Methyl morpholine are dropped into the solution, the temperature raised up to −2° C. (Bath temperature: −15° C.) To complete the anhydride building, the thin fluid suspension was stirred for 30 minutes at −5° C. Then the suspension is cooled to −10° C., followed by the addition of a prepared solution from 5.24 ml (0.048 Mol) benzyl amine and 10 ml dichloromethane within 20 minutes in a temperature range of −10° C. to −5° C. The thin fluid suspension is stirred for further 1 h without cooling bath Tend: 11° C.

The suspension is extracted four times with:
10 ml Water
10 ml 5% Sodiumhydrogene carbonate
10 ml 1 M Hydrochloric acid
10 ml Water
The remaining product layer are evaporated to dryness. Residue: 9.36 g oily product (80%)

Example 2.2

Preparation of 2-amino-N-benzyl-3-methoxy-propionamide (IV) from N-Benzyl-2-chloro-3-methoxy-propionamide (Vb)

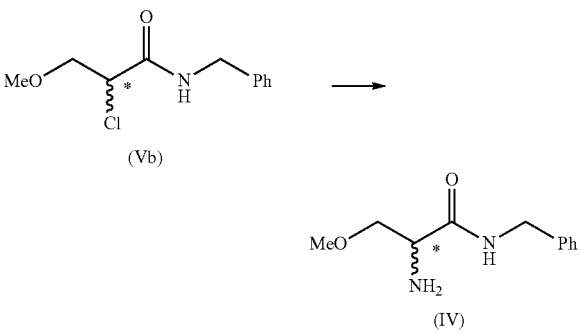

12.07 g N-Benzyl-2-chloro-3-methoxy-propionamide (Vb) are dissolved in 66 ml methanol. The solution is transferred into an autoklav and treated with 212 ml of 28% aq ammonia. The autoklav is closed and heated 2 h at 120° C. End pressure: 5.3 bar.

The solution is evaporated to dryness. The residue is taken up in 200 ml water and extracted twice with dichlorometane, to remove less polar impurities. The aqueous product layer is treated with 35% sodium hydroxide solution and extracted twice with dichloromethane. The dichloromethane layer is separated and evaporated to dryness.

Residue: 6.52 g brownish oil
Yield: 59%
LCMS: 91.6% [M+H] 209

Example 3

Preparation of Lacosamide from 2-amino-N-benzyl-3-methoxy-propionamide (IV)

Example 3.1

Diastereoisomeric Resolution of 2-amino-N-benzyl-3-methoxy-propionamide (IV) with Salts

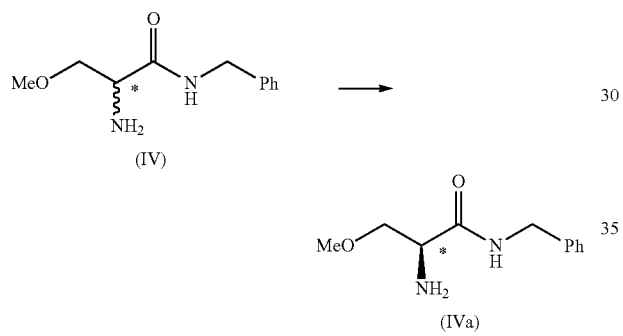

3.1.1. Resolution with (+)-(+)-O,O'-dibenzoyl tartaric acid 500 mg 2-amino-N-benzyl-3-methoxy-propionamide (IV) is dissolved at room temperature in 2.5 ml 1-propanol. In parallel, 430 mg (+)-(+)-O,O'-dibenzoyl tartaric acid is dissolved at room temperature in 2.5 ml 1-propanol. The salt solution is added at room temperature to the 2-amino-N-benzyl-3-methoxy-propionamide (IV)/1-propanol solution. 10 ml of the mixture are seeded at room temperature with crystals of (R)-2-amino-N-benzyl-3-methoxy-propionamide (IVa) and stirred for about 5 minutes. Thereby white, flaky crystals precipitated. These crystals are extracted.

320 mg of solid product is obtained from the solution (yield: 23.5%, chemical purity: 84%, chiral purity: 68% R-enantiomer and 32% S-enantiomer).

160 mg of said solid product are added to 4 ml of 1-propanol and dissolved in a water quench at a temperature of about 85° C. The mixture is cooled down and seeded as described before. White, flaky crystals are extracted after about 5 minutes at room temperature (yield: 55 mg, 34%, chemical purity 96%, chiral purity 26% S-enantiomer; 74% R-enantiomer (IVa)). The 55 mg are added to 1 ml 1-propanol and dissolved in a water quench at a temperature of about 85° C. The mixture is cooled down to room temperature. No seeding is required. Precipitated, white crystals can be extracted after 5 to 10 minutes stirring (yield: 30 mg, 75%, chemical purity 98.3%, chiral purity 15% S-enantiomer and 85% R-enantiomer (IVa).

3.1.2. Resolution with N-acetyl-D-leucine

To 6 g of 2-amino-N-benzyl-3-methoxy-propionamide (IV) is added 4.99 g of N-acetyl-D-leucine in 30 mL of isopropylacetate. The suspension is heated to 85° C. for 1 hour and then filtered at 80° C. (yield: 5.06 g, 46.5%; chiral purity: 80.5% R-enantiomer (IVa), 19.5% S-enantiomer). 2 g of this salt are heated to 85° C. in 10 mL isopropylacetate for 1 hour and then filtered at 80° C. (yield: 1.14 g, 57.25%, chiral purity: 97.5% R-enantiomer (IVa), 2.5% S-enantiomer)

Example 3.2

Preparation of (R)-2-acetamido-N-benzyl-3-methoxypropionamide (I) from (R)-2-amino-N-benzyl-3-methoxy-propionamide (IVa)

1.12 g (R)-2-amino-N-benzyl-3-methoxy-propionamide (IVa) (0.0054 mol) is dissolved in 25 ml of dichloromethane. After adding 0.756 ml acetic anhydride (0.8167 g, 0.08 mol), the mixture was stirred for 2 hours at room temperature. Subsequently, the mixture was consecutively extracted with 5 ml water, 5 ml 1M hydrochloric acid, 5 ml 5% sodiumhydrogencarbonate-solution and 5 ml water. The organic product phase is evaporated (HPLC: R-Isomer: 93.46% (I), S-Isomer: 6.54% (III)).

Example 4

Preparation of 2-acetamido-N-benzyl-3-methoxypropionamide (II) from N-acetyl-O-methyl-D,L-serine

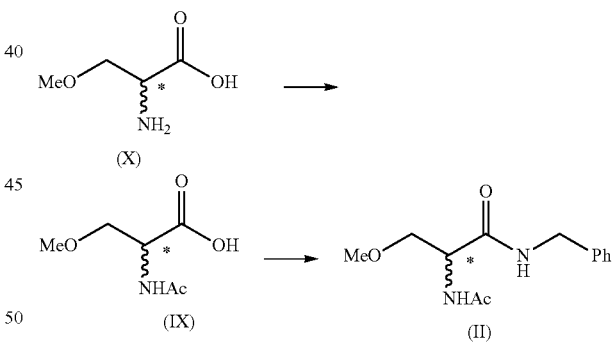

Example 4.1

Preparation of N-acetyl-O-methyl-D,L-serine (IX)

In a vessel, equipped with a mechanical stirrer, add at 20° C., 1.0 eq. of O-methyl-D,L-serine. Add 6 volumes of tetrahydrofuran and 0.65 volume of water. Add dropwise in 5 minutes 1.2 eq. of acetic anhydride. Stir mechanically the white suspension until complete conversion (HPLC monitoring, typical reaction time: 16 hours). At the end of the reaction the mixture becomes homogenous. Remove tetrahydrofuran as well as water azeotropically. Add toluene in order to remove completely water and acetic acid (KF and GC control). Crystallize the obtained crude solid in 6 volumes of acetone. Dry the wet solid at 40° C. under vacuum overnight. N-acetyl-O-methyl-D,L-serine (IX) is obtained as a white solid in 80% yield with a chemical purity of greater than 99% measured by HPLC.

The NMR spectrum obtained is consistent with caracteristics described for compound (IX) in the literature (S. V. Andurkar et al., Tetrahedron: Asymmetry 9, 3841-3854).

Example 4.2

Preparation of 2-acetamido-N-benzyl-3-methoxypropion-amide (II) from N-acetyl-O-methyl-D,L-serine (IX)

Example 4.2.1

Use of isobutylchloroformiate and N-methylmorpholine

In a reaction vessel equipped with a mechanical stirrer were charged 1.0 eq. of N-acetyl-O-methyl-D,L-serine (IX) and 10 volumes of anhydrous THF. After cooling down to −20° C., 1.15 eq. of isobutylchloroformiate and then 1.15 eq. of N-methylmorpholine were successively added dropwise maintaining the temperature below −15° C. The reaction mixture was stirred further 15 min. at −20° C. and then 1.15 eq. of benzylamine were added dropwise maintaining the mass temperature below −15° C. After further 15 min stirring, the mixture was allowed to warm up to room temperature and salts were removed by filtration. The filtrate was concentrated to dryness under vacuum and the residual solid was recrystallized in ethyl acetate. The crystals obtained are dried overnight under vacuum at a temperature of 50° C.

Compound (II) is obtained in 62% yield and a purity of 99.6%.

Example 4

2.2. Use of Anhydrous Boric Acid

In a reaction vessel equipped with a Dean-Stark apparatus, a mechanical stirrer and a thermometer probe, add 1.0 eq. of N-acetyl-O-methyl-D,L-serine (IX) and 8 volumes of toluene. Add 0.1 eq. of anhydrous boric acid and 1 eq. of benzylamine. Heat the suspension at reflux for 16 hours with continuous removal of water with the Dean-Stark apparatus. At the end of the reaction, the reaction mixture is homogeneous. Add 1 volume of water and gradually cool the reaction mixture to 0° C. Filter under vacuum on a sintered glass filter. Rinse with the minimum of water and toluene. Dry the wet solid at 40° C. under vacuum overnight.

2-acetamido-N-benzyl-3-methoxypropion-amide (II) is obtained in a yield of 65% with a chemical purity greater than 99% measured by HPLC. The NMR spectra is consistent with the one obtained with a reference sample of Lacosamide.

4.2.3. By the Use of triphenylboroxine as Catalyst

In a reaction vessel equipped with a Dean-Stark apparatus, a mechanical stirrer and thermometer probe, were charged 1.0 eq. of N-acetyl-O-methy-D,L-serine (IX) and 8 volumes of toluene. 0.6 eq. of phenylboronic acid (or 0.2 eq. of the corresponding triphenylboroxine) was added and the reaction mixture was heated to reflux. 1 eq. of benzylamine was then added continuously over 2 hours and the reaction mixture was maintained further 22 hours at reflux. After complete conversion, the mixture was cooled to 75° C., and 3 volumes of ethyl acetate were added. The homogenous mixture was cooled to 60° C. and seeded with 1% w:w of (II). The crystallization was allowed to develop at this T° and the mixture was filtered at 0° C., rinsed with a mixture of fresh toluene/ethyl acetate (70:30) and dried under vacuum for 24 hours.

Compound (II) is obtained in 70% yield and a chemical purity greater than 94.5%.

4.2.4. Use of diisopropylcarbodiimide

Into a suspension of 1.0 eq. of N-acetyl-O-methyl-D,L-serine in 10 volumes of dichloromethane was added dropwise at 15° C. a solution of 1.2 eq. of diisopropylcarbodiimide (DIC) in 1 volume of dichloromethane. The mixture was stirred 2 hours at 20° C. and then cooled down to 0° C. and stirred further 1 hour. The 1,3-diisopropylurea was filtered off and 1.05 eq. of benzylamine were added dropwise to the resulting filtrate maintaining the temperature below 20° C. After complete conversion, the solution was then evaporated to dryness leading to the crude material which was then further crystallized in ethyl acetate.

Compound (II) was obtained with 78.2% yield and purity greater than 98.8%.

The invention claimed is:

1. A process for the manufacture of substantially optically pure (R)-2-acetamido-N-benzyl-3-methoxypropion-amide (I) consisting essentially of:
   (a) resolving 2-acetamido-N-benzyl-3-methoxypropion-amide (II) into (R)-2-acetamido-N-benzyl-3-methoxypropion-amide (I) and (S)-2-acetamido-N-benzyl-3-methoxypropionamide (III);
   (b) racemizing (S)-2-acetamido-N-benzyl-3-methoxypropion-amide (III) thereby obtained;
   (c) further resolving the resulting 2-acetamido-N-benzyl-3-methoxypropion-amide (II); and
   (d) combining the (R)-2-acetamido-N-benzyl-3-methoxypropion-amide (I) of (a) and (c).

2. The process according to claim 1 wherein the resolution is performed by Chiral chromatographic separation using a chiral stationary phase (CSP) and a mobile phase.

3. The process according to claim 2 wherein the chiral chromatographic separation is performed by Multiple Column Chromatography (MCC).

4. The process according to claim 2 wherein the Chiral Stationary Phase (CSP) is a polysaccharide chiral selector coated or immobilized on a silica backbone.

5. The process according to claim 4 wherein the polysaccharide chiral selector is selected from cellulose tris(4-methylbenzoate), cellulose tribenzoate, amylose tris(3,5-dimethylphenylcarbamate) cellulose tris(3,5-dimethylphenylcarbamate), cellulose tris(4-methylphenylcarbamate) cellulose tris (3,5-dichlorophenylcarbamate), amylose tris [(S)-α-methylbenzylcarbamate]and cellulose tris(3-chloro-4-methylphenylcarbamate).

6. The process according to claim 2 wherein the mobile phase is selected from heptane, hexane, methanol, ethanol, iso-propanol, n-propanol, acetonitrile, isopropyl acetate, ethyl acetate, dichloromethane, chloroform, methyl t-butyl ether and mixtures thereof.

7. The process according to claim 6 wherein the mobile phase is a mixture of ethyl acetate and methanol or acetonitrile.

8. The process according to claim 1 wherein the racemisation is performed by reacting (S)-2-acetamido-N-benzyl-3-methoxypropion-amide (III) with a base selected from sodium methoxide, potassium hydroxide, sodium hydroxide, potassium carbonate, sodium carbonate, triethylamine, 1,8-Diazabicyclo[5.4.0]undec-7-ene and strong or weakly basic anion exchange resins.

9. The process according to claim 8 wherein the base is selected from sodium methoxide, potassium hydroxide, sodium hydroxide, potassium carbonate and sodium carbonate.

10. The process according to claim 8 which is performed at a temperature comprised between 20° C. and 80° C.

11. The process according to claim 8 which is performed in a solvent selected from methanol, ethanol, tetrahydrofuran, 2-methyl-tetrahydrofuran and acetonitrile.

12. The process according to claim 1 further comprising synthesizing 2-acetamido-N-benzyl-3-methoxypropion-amide (II) as follows:
reacting a compound of formula (VIa),

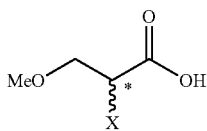
(VIa)

wherein X is a leaving group, with an alkylhaloformiate in the presence of a base and benzylamine;
(ii) performing ammonolysis of compound (V) resulting from step (i), wherein X is as defined in compound (VIa);

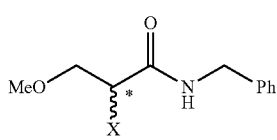
(V)

(iii) acetylating compound of formula (IV) thereby obtained

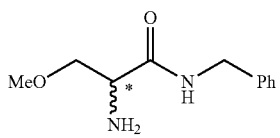
(IV)

with acetic anhydride in a solvent;
(iv) isolating compound of formula (II).

13. The process according to claim 12 wherein compound of formula (VIIIa), wherein X is a leaving group and R is a $C_{1-10}$ alkyl is formed in situ in step (i) before reaction with benzylamine

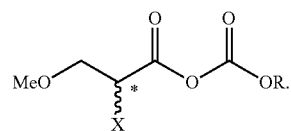
(VIIIa)

14. The process according to claim 12 wherein X is a halogen.

15. The process according to claim 12 wherein compound (VIa) is generated in situ by reacting 2,3-dibromo ethyl propionate (VIIa) or 2,3-dibromo methyl propionate (VIIb) with sodium methoxide in methanol at a temperature lower than 10° C.

16. The process according to claim 12 wherein step (ii) is performed with an excess of aqueous ammonia in the presence of methanol.

17. The process according to any claim 12 wherein step (iii) is performed at a temperature comprised between 50° C. and 70° C.

18. A process of manufacture of substantially optically pure (R)-2-acetamido-N-benzyl-3-methoxypropion-amide (I) comprising:
(i) reacting 2,3-dibromo ethyl propionate (VIIa) or 2,3-dibromo methyl propionate (VIIb)

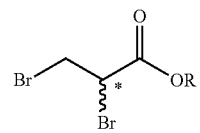

R = Et (VIIa)
R = Me (VIIb)

with sodium methoxide in methanol in the presence of an alkylchloroformiate followed by benzylamine to afford 2-bromo-N-benzyl-3-methoxypropion-amide (Va)

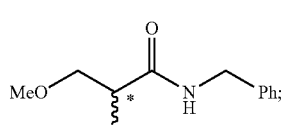
(Va)

(ii) reacting 2-bromo-N-benzyl-3-methoxypropion-amide (Va) with aqueous ammonia to afford 2-amino-N-benzyl-3-methoxypropion-amide (IV)

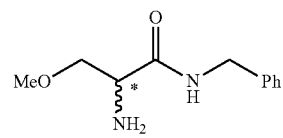
(IV)

(iii) acetylating 2-amino-N-benzyl-3-methoxypropion-amide (IV) with acetic anhydride in a solvent to afford 2-acetamido-N-benzyl-3-methoxypropion-amide (II)

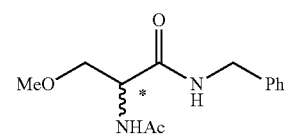
(II)

(iv) isolating compound of formula (II);
(v) resolving isolated 2-acetamido-N-benzyl-3-methoxypropion-amide (II) into (R)-2-acetamido-N-benzyl-3-methoxypropion-amide (I) and (S)-2-acetamido-N-benzyl-3-methoxypropion-amide (III)

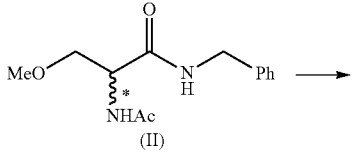
(II)

-continued

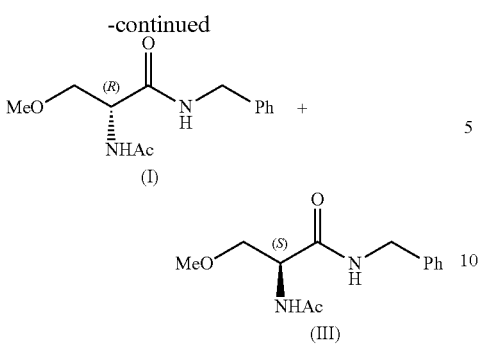

(vi) racemizing (S)-2-acetamido-N-benzyl-3-methoxypropion-amide (III) thereby obtained; and
(vii) further resolving resulting 2-acetamido-N-benzyl-3-methoxypropion-amide (II)

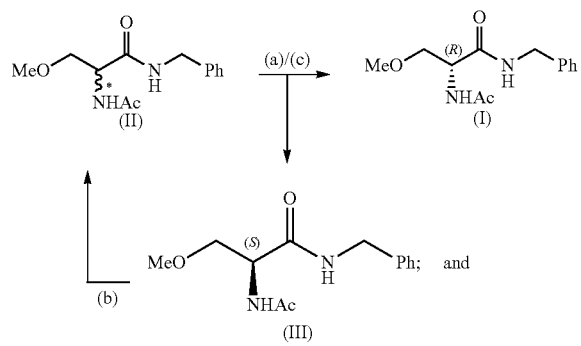

(viii) combining the (R)-2-acetamido-N-benzyl-3-methoxypropion-amide (I) of (v) and (vii).

19. The process according to claim 1 wherein 2-acetamido-N-benzyl-3-methoxypropion-amide (II) is manufactured according to the following steps:
(i) acetylation of O-Methyl-D,L-serine (X)

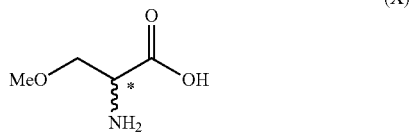

(ii) reacting 2-acetamido-3-methoxypropionate (IX) thereby obtained

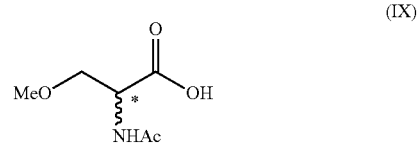 [SMILES: COCC(NC(C)=O)C(=O)O]

with benzyl amine
(iii) isolating compound of formula (II).

20. The process according to claim 19 wherein step (i) is performed in the presence of acetic anhydride in a solvent selected from the group consisting of acetic acid, toluene, tetrahydrofuran, 2-methyl-tetrahydrofuran, isobutylacetate, dichloromethane, water and mixtures thereof.

21. The process according to claim 19 wherein step (ii) is performed in the presence of a catalyst selected from the group consisting of boric acid, phenylboronic acid, 3,4,5-trifluorophenylboronic acid, 2-(N,N-di-isopropylaminomethyl)phenylboronic acid and 2-(N,N-dimethylaminomethyl)phenylboronic acid.

22. The process according to claim 19 wherein step (ii) is performed in the presence of dicyclohexyl- (DCC) or diisopropylcarbodiimide (DIC) in a solvent selected from the group consisting of tetrahydrofuran, ethyl acetate and dichloromethane.

23. The process according to claim 19 wherein step (ii) is performed at reflux temperature of a solvent selected from the group consisting of toluene, N-methylpyrrolidone and mixtures thereof, tetrahydrofuran, 2-methyl-tetrahydrofuran, cyclopentylmethyl ether, di n-butylether and fluorobenzene.

24. The process according to claim 14 wherein the halogen is bromine.

\* \* \* \* \*